(12) United States Patent
Loria et al.

(10) Patent No.: US 7,927,600 B2
(45) Date of Patent: Apr. 19, 2011

(54) ANTI-ALLERGIC PHARMACEUTICAL COMPOSITION CONTAINING AT LEAST ONE ALLERGEN AND AT LEAST ONE ANTIHISTAMINE COMPOUND

(76) Inventors: Emile Loria, La Jolla, CA (US); Gaetan Terrasse, Saint-Valier (FR); Yves Trehin, Toulouse (FR)

(*) Notice: Subject to any disclaimer, the term of this patent is extended or adjusted under 35 U.S.C. 154(b) by 328 days.

(21) Appl. No.: 11/413,489

(22) Filed: Apr. 28, 2006

(65) Prior Publication Data

US 2007/0003580 A1 Jan. 4, 2007

Related U.S. Application Data

(63) Continuation-in-part of application No. 09/867,159, filed on May 29, 2001, now Pat. No. 7,048,928.

(30) Foreign Application Priority Data

Mar. 30, 2001 (FR) .................................. 01 04370
May 3, 2001 (FR) .................................. 01 05929

(51) Int. Cl.
*A61K 39/36* (2006.01)
*A61K 38/03* (2006.01)
*A61K 38/43* (2006.01)
*C07K 4/10* (2006.01)
*C07K 14/415* (2006.01)
*C12N 15/29* (2006.01)

(52) U.S. Cl. .................... 424/185.1; 424/275.1; 514/44; 536/23.6

(58) Field of Classification Search ........................ None
See application file for complete search history.

(56) References Cited

U.S. PATENT DOCUMENTS

| 4,302,458 A * | 11/1981 | Chazerain et al. ............ 514/307 |
| 5,256,680 A * | 10/1993 | Connor et al. ................ 514/364 |
| 5,433,948 A * | 7/1995 | Thomas et al. ............ 424/185.1 |
| 5,820,862 A * | 10/1998 | Garman et al. ............ 424/184.1 |
| 5,872,852 A * | 2/1999 | Dougherty .................... 381/57 |
| 6,258,816 B1 * | 7/2001 | Singh et al. ............... 514/255.04 |
| 6,319,513 B1 * | 11/2001 | Dobrozsi ..................... 424/434 |
| 6,455,686 B1 * | 9/2002 | McCall et al. ............... 536/23.4 |
| 2004/0166123 A1 * | 8/2004 | Jacobi et al. ............... 424/275.1 |

OTHER PUBLICATIONS

Whisstock et al, Quarterly Reviews of Biophysics 36(3): 307-340, 2003.*
Fasler et al, J Allergy Clin Immunology 101(4): 521-530, Apr. 1998.*
Hsu et al, Int Immunol 8(9); 1405-11, Sep. 1996.*
Hoyne et al, Immunology and Cell Biology 74: 180-186, 1996.*
Cohen, Stanley N. et al., "Nonchromosomal Antibiotic Resistance in Bacteria: Genetic Transformation of *Escherichia coli* by R-Factor DNA," *Proc. Nat. Acad. Sci. USA*, 1972, 69:2110-4. (Exhibit 1).
Crapo, R. O. et al., "Difference in Spirometry Reference Values: A Statistical Comparison of a Mongolian and Caucasian Study," *European Respiratory Journal.*, 1999, 13:606-9. (Exhibit 2).
Graham, F.L. and A.J. Van Der Eb, "A New Technique for the Assay of Infectivity of Human Adenovirus 5 DNA," *Virology*, 1973, 52:456-67. (Exhibit 3).
Southern, E. M., "Detection of Specific Sequences Among DNA Fragments Separated by Gel Electrophoresis," *Journal of Molecular Biology*, 1975, 98:503-17. (Exhibit 4).
Wigler, Michael et al., "DNA-mediated Transfer of the Adenine Phosphoribosyltransferase Locus into Mammalian Cells," *Proc. Natl. Acad. Sci. USA*, 1979, 76:1373-6. (Exhibit 5).
Berent, Susan L. et al., "Comparison of Oligonucleotide and Long DNA Fragments as Probes in DNA and RNA Dot, Southern, Northern, Colony and Plaque Hybridizations," *Bio Techniques*, 1985, 208-20. (Exhibit 6).
Southern, P.J. and P. Berg, "Transformation of Mammalian Cells to Antibiotic Resistance with a Bacterial Gene Under Control of the SV40 Early Region Promoter," Molecular and Applied Genetics, 1982, 1:327-41. (Exhibit 7).

* cited by examiner

*Primary Examiner* — Phuong Huynh
(74) *Attorney, Agent, or Firm* — Adriano & Associates

(57) ABSTRACT

The present invention relates to an anti-allergic pharmaceutical composition containing at least two active agents chosen from: (i) one allergen, (ii) one antihistamine compound, and (iii) one inhibitor of histamine synthesis, said active agents being associated in said composition with a pharmaceutically acceptable vehicle.

5 Claims, No Drawings

SEQUENCE LISTING

```
<160> NUMBER OF SEQ ID NOS: 7

<210> SEQ ID NO 1
<211> LENGTH: 666
<212> TYPE: DNA
<213> ORGANISM: Dermatophagoides pteronyssinus

<400> SEQUENCE: 1
actaacgcct gcagtatcaa tggaaatgct ccagctgaaa tcgatttgcg acaaatgcga     60
actgtcactc ccattcgtat gcaaggaggc tgtggttcat gttgggcttt ctctggtgtt    120
gccgcaactg aatcagctta tttggctcac cgtaatcaat cattggatct tgctgaacaa    180
gaattagtcg attgtgcttc ccaacacggt tgtcatggtg ataccattcc acgtggtatt    240
gaatacatcc aacataatgg tgtcgtccaa gaaagctact atcgatacgt tgcacgagaa    300
caatcatgcc gaccaccaaa tgcacaacgt ttcggtatct caaactattg ccaaatttac    360
ccaccaaatg caaacaaaat tcgtgaagct ttggctcaaa cccacagcgc tattgccgtc    420
attattggca tcaaagattt agacgcattc cgtcattatg atggccgaac aatcattcaa    480
cgcgataatg gttaccaacc aaactatcac gctgtcaaca ttgttggtta cagtaacgca    540
caaggtgtcg attattggat cgtacgaaac agttgggata ccaattgggg tgataatggt    600
tacggttatt ttgctgccaa catcgatttg atgatgattg aagaatatcc atatgttgtc    660
attctc                                                               666

<210> SEQ ID NO 2
<211> LENGTH: 222
<212> TYPE: PRT
<213> ORGANISM: Dermatophagoides pteronyssinus
<220> FEATURE:
<221> NAME/KEY: PEPTIDE
<222> LOCATION: (1)..(222)
<223> OTHER INFORMATION: Peptide sequence from cystine protease.

<400> SEQUENCE: 2

Thr Asn Ala Cys Ser Ile Asn Gly Asn Ala Pro Ala Glu Ile Asp Leu
1               5                   10                  15

Arg Gln Met Arg Thr Val Thr Pro Ile Arg Met Gln Gly Gly Cys Gly
            20                  25                  30

Ser Cys Trp Ala Phe Ser Gly Val Ala Ala Thr Glu Ser Ala Tyr Leu
        35                  40                  45
```

```
Ala His Arg Asn Gln Ser Leu Asp Leu Ala Glu Gln Glu Leu Val Asp
    50                  55                  60

Cys Ala Ser Gln His Gly Cys His Gly Asp Thr Ile Pro Arg Gly Ile
65                  70                  75                  80

Glu Tyr Ile Gln His Asn Gly Val Val Gln Glu Ser Tyr Tyr Arg Tyr
                85                  90                  95

Val Ala Arg Glu Gln Ser Cys Arg Arg Pro Asn Ala Gln Arg Phe Gly
            100                 105                 110

Ile Ser Asn Tyr Cys Gln Ile Tyr Pro Pro Asn Ala Asn Lys Ile Arg
        115                 120                 125

Glu Ala Leu Ala Gln Thr His Ser Ala Ile Ala Val Ile Ile Gly Ile
    130                 135                 140

Lys Asp Leu Asp Ala Phe Arg His Tyr Asp Gly Arg Thr Ile Ile Gln
145                 150                 155                 160

Arg Asp Asn Gly Tyr Gln Pro Asn Tyr His Ala Val Asn Ile Val Gly
                165                 170                 175

Tyr Ser Asn Ala Gln Gly Val Asp Tyr Trp Ile Val Arg Asn Ser Trp
            180                 185                 190

Asp Thr Asn Trp Gly Asp Asn Gly Tyr Gly Tyr Phe Ala Ala Asn Ile
        195                 200                 205

Asp Leu Met Met Ile Glu Glu Tyr Pro Tyr Val Val Ile Leu
    210                 215                 220

<210> SEQ ID NO 3
<211> LENGTH: 10
<212> TYPE: PRT
<213> ORGANISM: Dermatophagoides pteronyssinus
<220> FEATURE:
<221> NAME/KEY: PEPTIDE
<222> LOCATION: (1)..(10)
<223> OTHER INFORMATION: Comprises epitope from cystine protease.

<400> SEQUENCE: 3

Arg Met Gln Gly Gly Cys Gly Ser Cys Asn
1               5                   10

<210> SEQ ID NO 4
<211> LENGTH: 10
<212> TYPE: PRT
<213> ORGANISM: Dermatophagoides pteronyssinus
<220> FEATURE:
<221> NAME/KEY: peptide
<222> LOCATION: (1)..(10)
<223> OTHER INFORMATION: Comprises epitope from cystine protease.

<400> SEQUENCE: 4

Gln Pro Asn Tyr His Ala Val Asn Ile Val
1               5                   10

<210> SEQ ID NO 5
<211> LENGTH: 9
<212> TYPE: PRT
<213> ORGANISM: Dermatophagoides pteronyssinus
<220> FEATURE:
<221> NAME/KEY: peptide
<222> LOCATION: (1)..(9)
<223> OTHER INFORMATION: Comprises epitope from cystine protease.

<400> SEQUENCE: 5

Trp Thr Val Arg Asn Ser Trp Asp Thr
1               5
```

```
<210> SEQ ID NO 6
<211> LENGTH: 9
<212> TYPE: DNA
<213> ORGANISM: Dermatophagoides pteronyssinus
<220> FEATURE:
<221> NAME/KEY: primer
<222> LOCATION: (1)..(9)
<223> OTHER INFORMATION:

<400> SEQUENCE: 6 gcggcggcg                                                                        9

<210> SEQ ID NO 7
<211> LENGTH: 12
<212> TYPE: DNA
<213> ORGANISM: Dermatophagoides pteronyssinus
<220> FEATURE:
<221> NAME/KEY: primer
<222> LOCATION: (1)..(12)
<223> OTHER INFORMATION:

<400> SEQUENCE: 7
tgagcggcgg cg                                                                   12
```

ANTI-ALLERGIC PHARMACEUTICAL COMPOSITION CONTAINING AT LEAST ONE ALLERGEN AND AT LEAST ONE ANTIHISTAMINE COMPOUND

This application is a continuation-in-part of U.S. application Ser. No. 09/867,159, filed May 29, 2001, which claims the priority of French Application No. 01/04370 filed Mar. 30, 2001 and French Application No. 01/05929 filed May 3, 2001, the contents of which are hereby incorporated by reference, in their entirety, into this application, and from which priority is hereby claimed.

Throughout this application various publications are referenced. The disclosures of these publications in their entireties are hereby incorporated by reference into this application in order to more fully describe the state of the art to which the invention pertains.

BACKGROUND OF THE INVENTION

The present invention relates to new pharmaceutical compositions for the prevention and treatment of allergies. Allergies are a scourge which affects 25% of the world's population. This number is on the increase in connection with growing environmental toxicity (dust, food, motor vehicles). In addition, a person's risk of suffering from allergy is increased if there is a previous family history of allergy.

The biological mechanism of allergies may be described as an abnormally amplified reaction to the entry of an allergen into the body. The following events account for the reaction:
  identification of the allergen by the body,
  secretion of cytokines in response to allergen penetration,
  conversion of Th1 cells into Th2 cells, with the production of clones specific to the antigen,
  the Th2 cells synthesize interleukins 4 and 13, responsible for aggravation of the allergic symptoms through an upsurge in IgE synthesis,
  the terminal phase of the reaction is the release of histamine and serotonin having a recruiting effect on the Th2 clones,
  toxic and inflammatory self-maintaining reaction, even without any antigen stimulation.

The antigen-presenting cells (APCs: macrophages, dendritic cells, B-lymphocytes) take part in the reaction of hypersensitivity through basic cell cooperation carrying the immune reaction further. Allergies belong to the nonself class of defense mechanisms. The main allergens are acarids (dust mites) (80%) and pollens (20%).

The self-stimulating reactions of specific APC clones have an effect on the general rate of release of histamine and serotonin leading to an aggravation of the general clinical symptomotology.

The recruitment level of new IgE-secreting cells is thereby increased facilitating the explosion of clinical signs when a new allergen penetrates inside the body. This can be seen in atopic persons in whom allergic reactions are severe owing to the high level of Th2 clones promoting the synthesis of IgE.

The general reaction observed subsequent to the penetration of the new allergen is not due to its toxicity but simply to the fact that the triggering level of allergic phenomena is very low, helped by other sensitizations.

An allergy is a reaction due to hypersynthesis of IgE immunoglobulins. The inflammatory reaction chiefly affects the respiratory and ENT spheres, with pathological focalization at the nose, lungs and skin. Pathologies associated with the allergy are invalidating and suffer from the lack of efficacy of conventional treatment. There is no preventive strategy and curative means are insufficient or ill used.

The usual treatment of allergic disease consists, during a first phase, of identifying the allergen responsible: dust mites, pollen, mold, food. The second phase comprises removal measures. The third treatment phase focuses on the target organ which appears to be symptomatic: ENT treatment for rhinitis, anti-asthmatic treatment if the affected sphere is respiratory, dermatological treatment if the affected areas are skin areas.

In the event of failure of the preceding measures, individual or complementary treatment may be offered through the choice of a specific immunotherapy (specific pollen, specific acarid, specific mould). The complexity of the treatment instituted often leads to poor patient compliance, and therefore, failure to the treatment.

The purpose of the present invention is precisely to offer new means of treating allergies that are both preventive and curative.

SUMMARY OF THE INVENTION

The present invention provides pharmaceutical compositions (e.g., in a semisolid or liquid dosage form) that are, e.g., anti-allergic. In one embodiment, the pharmaceutical composition comprises an allergen, and an antihistamine compound. In another embodiment, the pharmaceutical composition comprises an allergen and an inhibitor of histamine synthesis. In a further embodiment, the pharmaceutical composition comprises an antihistamine compound and an inhibitor of histamine synthesis. In a further embodiment, the pharmaceutical composition comprises an allergen, an antihistamine compound, and an inhibitor of histamine synthesis. Additionally, said pharmaceutical composition comprises a pharmaceutically acceptable carrier or vehicle.

Additionally, the present invention provides methods for inhibiting, preventing, or treating allergic symptoms comprising administering: (i) an allergen, and an antihistamine compound, (ii) an allergen and an inhibitor of histamine synthesis, (iii) an antihistamine compound and an inhibitor of histamine synthesis, or (iv) an allergen, an antihistamine compound, and an inhibitor of histamine synthesis.

The allergen, antihistamine compound, and inhibitor of histamine synthesis can be administered sequentially (in any order) or concurrently. Further, more than one allergen, antihistamine compound, and/or inhibitor of histamine synthesis can be used or administered.

DETAILED DESCRIPTION OF THE INVENTION

Compositions of the Invention

The present invention provides pharmaceutical compositions (e.g., anti-allergic compositions) containing two or more active agents of the invention chosen from among: (i) an allergen, (ii) an antihistamine compound, and (iii) an inhibitor of histamine synthesis (agents of the invention). Said agents of the invention may be associated in said composition with a pharmaceutically acceptable carrier or vehicle. Pharmaceutically acceptable carrier or vehicle refers to a non-toxic solid, semisolid (also referred to herein as softgel) or liquid filler, diluent, encapsulating material or formulation auxiliary of any type. The invention also provides methods for treating or preventing of allergy using said compositions.

A first preferred embodiment of an anti-allergic pharmaceutical composition according to the invention contains (i) at least one allergen and (ii) at least one antihistamine compound, in a pharmaceutically acceptable vehicle. A suitable example of an allergen is cystine protease. A suitable example of an antihistamine compound is an H1 antagonist. H1 antagonists include, but are not limited to, any or a combination of, brompheniramine, cetirizine, fexofenadine, cyproheptadine, dexchlorpheniramine, hydroxizine, ketotifen, loratadine, mequitazine, oxotomide, mizolastine, ebastine, astemizole, carbinoxamide, alimemazine, buclizine, cyclizine hydrochloride and doxylamine or analogs or equivalents thereof.

In another embodiment, the pharmaceutical composition comprises an allergen and an inhibitor of histamine synthesis. For example, in a particular embodiment, the allergen is cystine protease and the inhibitor of histamine synthesis is a histidine decarboxylase inhibitor (e.g., tritoqualine).

In a further embodiment, the pharmaceutical composition comprises an antihistamine compound and an inhibitor of histamine synthesis. For example, in a particular embodiment, the inhibitor of histamine synthesis is tritoqualine and the antihistamine compound is an H1 antagonist. The H1 antagonist may be any, or a combination of, brompheniramine, cetirizine, fexofenadine, cyproheptadine, dexchlorpheniramine, hydroxizine, ketotifen, loratadine, mequitazine, oxotomide, mizolastine, ebastine, astemizole, carbinoxamide, alimemazine, buclizine, cyclizine hydrochloride and doxylamine or analogs thereof.

In a further embodiment, the pharmaceutical composition comprises an allergen, an antihistamine compound, and an inhibitor of histamine synthesis. For example, in a particular embodiment, the allergen is cystine protease, the inhibitor of histamine synthesis is tritoqualine and the antihistamine compound is an H1 antagonist. The H1 antagonist may be any, or a combination of, brompheniramine, cetirizine, fexofenadine, cyproheptadine, dexchlorpheniramine, hydroxizine, ketotifen, loratadine, mequitazine, oxotomide, mizolastine, ebastine, astemizole, carbinoxamide, alimemazine, buclizine, cyclizine hydrochloride and doxylamine. Although not wishing to be bound by any theory, when administered to a subject, the composition may be metabolized thus enabling release of peptides from the allergen and other chemical substances from the composition in an independent manner at galenic (i.e., pharmaceutically effective dosage) level(s). The peptides so released can be complete or partial amino acid sequences (fragments) that are part of the allergen that can bind MHC molecules and trigger an immunological response.

Advantageously, said allergen may be chosen from among the major antigens or mixture of major antigens of acarids able to induce an immune reaction. Alternatively, the allergen may be a nucleic acid that encodes the major antigens or mixture of major antigens of acarids able to induce an immune reaction. Indeed, one embodiment of the invention involved using ubiquitous antigens of acarids. These antigens are present in substantial quantity in the environment and are the cause of the development of allergic reactions in the world. For example, two acarids, *Dermatogoides Pteronyssinus* (DP) and *Dermatogoides Farinae* (DF) are the most represented in the world environment.

In accordance with the invention, the allergens used in the compositions of the invention may either be extracts obtained from crude biological material (e.g., DerP1), or wholly or partly purified proteins or peptides optionally produced by genetic engineering or by any route of chemical synthesis. Extracts containing cystine protease may be purchased from Allermed (7203 Convoy Court, San Diego, Calif. 92111-1020), Stallergenes, S. A. (6, rue Alexis de Tocqueville 92183 Antony Cedex FRANCE), Allerbio (45, rue de Paradis 75010 Paris), Kiralya (Parc Biocitech 102 route de Noisy 93230 Romainville France). Indoor Biotechnologies, Inc. 1216 Harris Street, Charlottesville, Va. 22903.

In one embodiment, the allergen is cystine protease or immunogenic portions thereof. The cystine protease can be from a crude or purified extract of cystine protease from dust mite (e.g., DerP1, from Stallergen, 6, rue Alexis de Tocqueville 92183 Antony Cedex FRANCE). Alternatively, cystine protease can be made using recombinant technology from a variety of microorganisms such as *E. Coli* or yeast. Further, peptide portions of the cystine protease can be synthetically manufactured and can be used as a means of treatment. DNA sequences encoding cystine protease and/or peptide sequences thereof (epitope sequences) can be used therapeutically, e.g., as DNA vaccine.

Further, in accordance with the invention, the allergen can comprise a cystine protease (or portions thereof) of *Dermatogoides Pteronyssinus* (DP) and *Dermatogoides Farinae* (DF). Cystine protease of *Dermatogoides Pteronyssinus* (P) and *Dermatogoides Farinae* (DF) share 90% identity. Some of the epitope sequences (e.g., amino acid sequences that bind the MHC molecule) of the cystine protease of *D. Pteronyssinus* (DP) are shown in the list of appended sequences given respectively under numbers SEQ ID NO: 1 and SEQ ID NO:2. In accordance with the invention, cystine protease can be from sources other than dustmite. For example, cystine protease can be from pollen.

Also in accord with the invention, the allergen can be a peptide epitope of cystine protease or multiple peptide epitopes of cystine protease and/or related antigens. In preferred embodiments, three peptide epitopes have been identified which have the ability to induce tolerance (desensitization) to the natural antigen and/or reduce the general level of the immune response. These are the three peptides with the following sequences:

```
RMQGGCGSCN        (SEQ ID NO: 3)
QPNYHAVNIV        (SEQ ID NO: 4)
WTVRNSWDT         (SEQ ID NO: 5)
``` and their possible analogues.

These peptide epitopes (also referred to herein as epitope sequences) are commonly found in DF and DP and other allergens e.g. acarid pollen and other species and are identical since they are carriers of the enzyme function of cystine protease. Their lipophilicity and the fact that they tolerate the enzyme function, account for the fact that these peptide epitopes are constant from one species of acarid to another and that they are the site of a general immune response.

The sequences of the peptide epitopes cited above may contain supplementary amino acid sequences or substitutions facilitating their affinity and immunogenicity to the Major Histocompatibility Complex (MHC).

In accordance with the practice of this invention, the peptide epitopes of cystine protease of the invention (SEQ ID NOS: 3, 4, and/or 5) e.g., may have amino acid substitutions resulting in molecules which would retain the functional property of the original peptide epitopes of cystine protease, namely, the peptide epitopes of cystine protease having such substitutions will still retain the activity of peptide epitopes above. These amino acid substitutions include, but are not necessarily limited to, amino acid substitutions known in the art as "conservative".

For example, it is a well-established principle of protein chemistry that certain amino acid substitutions, referred to as "conservative amino acid substitutions," can frequently be made without altering either the conformation or the function of the molecule. Such changes include substituting any of isoleucine (I), valine (V), and leucine (L) for any other of these hydrophobic amino acids; aspartic acid (D) for glutamic acid (E) and vice versa; glutamine (Q) for asparagine (N) and vice versa; and serine (S) for threonine (T) and vice versa. Other substitutions can also be considered conservative, depending on the environment of the particular amino acid and its role in the three-dimensional structure of the protein. For example, glycine (G) and alanine (A) can frequently be interchangeable, as can alanine and valine (V).

Methionine (M), which is relatively hydrophobic, can frequently be interchanged with leucine and isoleucine, and sometimes with valine. Lysine (K) and arginine (R) are frequently interchangeable in locations in which the significant feature of the amino acid residue is its charge and the differing pK's of these two amino acid residues are not significant. Still other changes can be considered "conservative" in particular environments.

The invention gives special consideration to pharmaceutical compositions containing at least one of these peptides as an allergen.

Protein or peptide molecules, including the peptide epitopes of the invention, and their nucleic acid form (e.g., RNA form), may be used in the methods of the invention to induce tolerance to the natural antigen and/or reduce the general level of the immune response.

Encoding the epitopes and/or inclusion of the peptide epitope sequences (e.g., the peptide epitopes of cystine protease such as any of SEQ ID NOS: 3, 4, and/or 5) in a longer sequence makes it possible to improve presenting of the antigens to the T-lymphocytes by antigen presenting cells (APCs). This improved presentation will allow presentation of the antigens and epitopes by the T-lymphocytes to the MHC and thereby trigger the immune tolerance response. The antigens should previously be rearranged by the APCs. The simple epitope form does not allow rearrangement by the APCs since, as a general rule, only a protein or peptide longer than about 10 amino acids may be cut and presented by the APCs to the T-lymphocytes.

The present invention also provides pharmaceutical compositions (e.g., anti-allergic compositions) comprising a semisolid or liquid dosage form of tritoqualine and a plurality of particles which permit the semisolid or liquid dosage form of tritoqualine. The particles comprise, but are not limited to, fine particles such as the excipients disclosed herein, e.g., typical excipients for softgels.

In one embodiment, the semisolid or liquid dosage form of tritoqualine composition further comprises an H1 antagonist. In an additional embodiment, the tritoqualine composition further comprises an H1 antagonist and a cystine protease.

In one aspect, the present invention provides a pharmaceutical composition for the treatment of allergy comprising a semisolid or liquid dosage form of tritoqualine, wherein the composition is an administrable formulation that allows resorption of the tritoqualine into a subject. In one embodiment, the administrable formulation can be, e.g., an inhalant or a topically administrable formulation such as an ointment or cream.

Recombinant DNA Molecules Containing Nucleic Acids Encoding the Peptide Epitopes of Cystine Protease Also provided are recombinant DNA molecules (rDNAs) that contain a nucleic acid sequence encoding a peptide epitope of cystine protease as herein described, or a fragment thereof as the allergen in the compositions of the invention and for use in the methods of the invention.

As used herein, a rDNA molecule is a DNA molecule that has been subjected to molecular manipulation in vitro. Methods for generating rDNA molecules are well known in the art, for example, see Sambrook et al., *Molecular Cloning* (1989). In the preferred rDNA molecules of the present invention, a nucleic acid sequence encoding a peptide epitope of cystine protease or a fragment thereof, is operably linked to one or more expression control sequences and/or vector sequences. The rDNA molecule can encode either an entire peptide epitope of cystine protease, or can encode a fragment thereof. Additionally, the rDNA can encode a protein comprising an entire peptide epitope of cystine protease or a fragment thereof (also referred to herein as an epigen).

The choice of vector and/or expression control sequences to which a nucleic acid sequence encoding a peptide epitope of cystine protease is operably linked depends directly, as is well known in the art, on the functional properties desired, e.g., protein expression, and the host cell to be transformed. A vector contemplated by the present invention is at least capable of directing the replication or insertion into the host chromosome, and preferably also expression, of a nucleic acid sequence encoding a peptide epitope of cystine protease included in the rDNA molecule.

Expression control elements that are used for regulating the expression of an operably linked protein encoding sequence are known in the art and include, but are not limited to, inducible promoters, constitutive promoters, secretion signals, enhancers, transcription terminators and other regulatory elements. Preferably, an inducible promoter that is readily controlled, such as being responsive to a nutrient in the host cell's medium, is used.

In one embodiment, the vector containing a nucleic acid sequence encoding a peptide epitope of cystine protease will include a prokaryotic replicon, i.e., a DNA sequence having the ability to direct autonomous replication and maintenance of the recombinant DNA molecule intrachromosomally in a prokaryotic host cell, such as a bacterial host cell, transformed therewith. Such replicons are well known in the art. In addition, vectors that include a prokaryotic replicon may also include a gene whose expression confers a detectable marker such as a drug resistance. Typical bacterial drug resistance genes are those that confer resistance to ampicillin or tetracycline.

Vectors that include a prokaryotic replicon can further include a prokaryotic or viral promoter capable of directing the expression (transcription and translation) of the peptide epitopes of cystine protease-encoding sequence in a bacterial host cell, such as *E. coli*. A promoter is an expression control element formed by a DNA sequence that permits binding of RNA polymerase and transcription to occur. Promoter sequences compatible with bacterial hosts are typically provided in plasmid vectors containing convenient restriction sites for insertion of a DNA segment of the present invention. Various viral vectors well known to those skilled in the art may also be used, such as, for example, a number of well known retroviral vectors.

Expression vectors compatible with eukaryotic cells, preferably those compatible with vertebrate cells, can also be used to variant rDNA molecules that contain a nucleic acid sequence encoding a peptide epitope of cystine protease. Eukaryotic cell expression vectors are well known in the art and are available from several commercial sources. Typically, such vectors are provided containing convenient restriction sites for insertion of the desired DNA segment.

Vectors suitable for use in the methods of the present invention are, without limitation, viral vectors including adenoviruses, lentivirus, retroviral vectors, adeno-associated viral (AAV) vectors.

Eukaryotic cell expression vectors used to construct the rDNA molecules of the present invention may further include a selectable marker that is effective in an eukaryotic cell, preferably a drug resistance selection marker. A preferred drug resistance marker is the gene whose expression results in neomycin resistance, i.e., the neomycin phosphotransferase (neo) gene (Southern et al., *J Mol Anal Genet* (1982) 1:327-341). Alternatively, the selectable marker can be present on a separate plasmid, and the two vectors are introduced by cotransfection of the host cell, and selected by culturing in the presence of the appropriate drug for the selectable marker.

In accordance with the practice of the invention, the vector can be a plasmid, cosmid or phage vector encoding the cDNA molecule discussed above. Additionally, the invention provides a host-vector system comprising the plasmid, cosmid or phage vector transfected into a suitable eukaryotic host cell. Examples of suitable eukaryotic host cells include a yeast cell, a plant cell, or an animal cell, such as a mammalian cell. The host-vector system is useful for the production of any of the peptide epitopes of cystine protease. Alternatively, the host cell can be prokaryotic, such as a bacterial cell.

Transformed Host Cells

The invention further provides host cells transformed with a nucleic acid molecule that encodes a peptide epitope of cystine protease or a fragment thereof. The host cell can be either prokaryotic or eukaryotic. Eukaryotic cells useful for expression of a peptide epitope of cystine protease are not limited, so long as the cell line is compatible with cell culture methods and compatible with the propagation of the expression vector and expression of a gene encoding a peptide epitope of cystine protease. Preferred eukaryotic host cells include, but are not limited to, yeast, insect and mammalian cells, preferably vertebrate cells such as those from a mouse, rat, monkey or human fibroblastic cell line. Any prokaryotic host can be used to express a rDNA molecule having a nucleic acid sequence encoding a peptide epitope of cystine protease.

Transformation of appropriate cell hosts with an rDNA molecule of the present invention is accomplished by well known methods that typically depend on the type of vector used and host system employed. With regard to transformation of prokaryotic host cells, electroporation and salt treatment methods are typically employed, see, for example, Cohen et al., *Proc Acad Sci USA* (1972) 69:2110; and Maniatis et al., *Molecular Cloning, A Laboratory Manual*, Cold Spring Harbor Laboratory, Cold Spring Harbor, N.Y. (1982). With regard to transformation of vertebrate cells with vectors containing rDNAs, electroporation, cationic lipid or salt treatment methods are typically employed, see, for example, Graham et al., *Virol* (1973) 52:456; Wigler et al., *Proc Natl Acad Sci USA* (1979) 76:1373-76.

Successfully transformed cells, i.e., cells that contain an rDNA molecule of the present invention, can be identified by well known techniques. For example, cells resulting from the introduction of an rDNA of the present invention can be cloned to produce single colonies. Cells from those colonies can be harvested, lysed and their DNA content examined for the presence of the rDNA using a method such as that described by Southern, *J Mol Biol* (1975) 98:503, or Berent et al., *Biotech* (1985) 3:208 or the proteins produced from the cell assayed via an immunological method.

Recombinant Methods of Generating the Peptide Epitopes of Cystine Protease

The invention further provides methods for producing the peptide epitopes of cystine protease using one of the nucleic acid molecules that encodes a peptide epitope of cystine protease described herein. In general terms, the production of the recombinant peptide epitopes of cystine protease typically can involve the following steps (Maniatis, supra).

First, a nucleic acid molecule is obtained that encodes a peptide epitope of cystine protease or a fragment thereof, such as the nucleic acid molecule depicted in SEQ ID NOS: 3, 4, and/or 5. The nucleic acid molecule is then preferably placed in an operable linkage with suitable control sequences, as described above, to generate an expression unit containing the peptide epitope of cystine protease-encoding sequence. The expression unit is used to transform a suitable host and the transformed host is cultured under conditions that allow the production of the peptide epitopes of cystine protease. Optionally the peptide epitopes of cystine protease is isolated from the medium or from the cells; recovery and purification of the protein may not be necessary in some instances where some impurities may be tolerated.

Each of the foregoing steps may be done in a variety of ways. For example, the desired coding sequences may be obtained from genomic fragments and used directly in an appropriate host. The construction of expression vectors that are operable in a variety of hosts is accomplished using an appropriate combination of replicons and control sequences. The control sequences, expression vectors, and transformation methods are dependent on the type of host cell used to express the gene and were discussed in detail earlier. Suitable restriction sites can, if not normally available, be added to the ends of the coding sequence so as to provide an excisable gene to insert into these vectors. A skilled artisan can readily adapt any host/expression system known in the art for use with sequences to produce the peptide epitopes of cystine protease.

These peptides may be associated with any pharmaceutically acceptable vector, of phospholipid type for example.

If epitopes are involved, the peptides may be primed by the following nucleotide sequence (corresponding to the gene): 5'GCGGCGGCG 3' (SEQ ID NO:6).

The controlled reaction of the TH2/TH1 switch induced by this allergen or its DNA may also be achieved using other methods, in particular with the nucleotide primers according to the following sequence 5'TGAGCGGCGGCG 3' (SEQ ID NO:7), and using any other method allowing upstream control of the TH2/TH1 switch.

It is therefore possible to integrate the DNA corresponding to the epitopes of DP/DF with a nucleotide primer sequence of sequence (SEQ ID NO:7) by alternating said sequence (SEQ ID NO:7) and an epitope such as to integrate the three major epitopes of DP/DF either together or separately.

The integration of the epitopes together leads to obtaining a group made up of a nucleotide primer sequence (SEQ ID NO:7) a first major epitope, a nucleotide primer sequence (SEQ ID NO:7), a second major epitope, a nucleotide primer sequence (SEQ ID NO:7), a third major epitope.

The integration of epitopes separately leads to mixing three groups each made up of a nucleotide primer sequence (SEQ ID NO:7) and a major epitope. This integration of the epitopes with a nucleotide primer sequence according to the following sequence (SEQ ID NO:7) improves the efficacy with which the DP/DF epigens are presented to the T-lymphocytes. With this improved presentation, the DP/DF epigens will stimulate the TH1 switch and therefore reduce the level of the allergic response.

The use firstly of these epitopes, and/or of a composition enabling the TH1/TH2 switch such as a composition comprising a DNA molecule comprising the nucleotide primers of sequence (SEQ ID NO:7), and secondly their association with an antihistamine compound and optionally with an inhibitor of histamine synthesis provide an efficient, innovative solution for the prevention and treatment of allergies.

Consequently, the compositions of the invention comprise an efficient quantity of at least one allergen, such as defined above without requiring that the selected allergen have a role in the particular patient's allergic reaction/symptomotology having to determine the role of this allergen in the patient's symptomotology.

With this approach it is possible to have global access to treating the allergic illness without giving consideration to the identity of the allergen that provided the allergic response or specificity of the allergen. Indeed with the composition of the invention it is possible to treat a level of immune reactivity and not to propose a specific immunotherapy.

The use of the allergen, under the different forms described above, in the compositions of the invention means that it is possible to induce tolerance to the natural antigen and to reduce the general level of immune response upstream. However, as mentioned previously, the allergen cannot alone cure the allergy since the toxic, inflammatory terminal reaction subsists which is self-maintaining without antigen stimulation. This reaction should also be treated by blocking the terminal phase of the allergy. Blocking the histamine receptors appears to be the main effector mechanism to achieve blocking. This blocking should be made over a time interval that is sufficiently long for there to be a negative feedback on the synthesis of these receptors. Antihistamines are anti-receptor molecules of choice to block this terminal reaction. Therefore, the compositions of the invention, in addition to the allergen, contain an antihistamine compound and optionally an inhibitor of histamine synthesis.

Examples of antihistamine compounds include, but are not limited to, brompheniramine, cetirizine, fexofenadine, cyproheptadine, dexchlorpheniramine, hydroxizine, ketotifen, loratidine, mequitazine, oxotomide, mizolastine, ebastine, astemizole, carbinoxamide, alimemazine, buclizine, cyclizine hydrochlorate, doxylamine.

As indicated above, the allergy is also accompanied by increased synthesis of histamine, which also causes self-maintenance of the terminal inflammatory reaction. This histamine synthesis may possibly be controlled, in order to improve the efficacy of the pharmaceutical composition of the invention. Consequently, the compositions of the invention contain an effective quantity of an antihistamine compound which may optionally be associated with an inhibitor of histamine synthesis in an amount sufficient to reduce synthesis of histamine. Therefore, blocking of the terminal histamine effector mechanisms will provide efficient control over the final cascade of the allergic reaction. The terminal route for the synthesis and stimulation of histamine receptors should therefore be blocked in global manner for the composition to have improved efficacy.

A particular form of implementation of the invention consists of an anti-allergic pharmaceutical composition containing at least one antihistamine compound and at least one inhibitor of histamine synthesis, associated with a pharmaceutically acceptable vehicle.

Inhibitors of histamine synthesis include, but are not limited to, an inhibitor of histidine decarboxylase such as tritoqualine.

The compositions of the invention provide a new allergen approach providing preventive vaccination against the development of allergic illnesses. The objective being to restore a silent defense homeostasis to the body in relation to its environment. The vaccines comprise the compositions of the invention, in a pharmacologically effective dose, and in a pharmaceutically acceptable formulation.

The production of these vaccines can be carried out according to known methods. Vaccination with these vaccines or combinations of vaccines according to the present invention can be carried out according to methods familiar to one skilled in the art (e.g. intradermally, intramuscularly, intraperitoneally, intravenously, subcutaneously or intranasally).

For intramuscular or subcutaneous administration, the vaccine can, for example, be suspended in physiological saline. For an intranasal or intraocular application, the vaccine can, e.g., be used in the form of a spray or an aqueous solution. For a local, e.g. oral, administration, it is often necessary to temporarily protect the compositions of the invention against inactivation, for example against proteolytic enzymes in the cavity of the mouth or in the stomach. Such temporary protection can be achieved by encapsulating the compositions, separately or together. This encapsulation can be carried out by coating with a protective agent (microencapsulation) or by embedding a multitude of the compositions of the invention (together or separate components) according to the present invention in a protective carrier (macroencapsulation).

The encapsulation material can be semipermeable or become semipermeable when introduced into the human or animal body. A biologically degradable substance is usually used as a carrier for the encapsulation.

The compositions of the invention may contain a quantity of allergens in the order of 1 to 1500 µg and advantageously from 10 to 150 µg. Concerning the peptides, each one is advantageously present in proportions in the region of 1 to 1500 µg so as to slow down the immunological response leading to increased IgE synthesis.

The antihistamine compound is present in the compositions of the invention in a proportion of the order of 1 to 2000 mg.

In the case of a composition according to the invention containing an antihistamine compound and an inhibitor of histamine synthesis, these compounds are present in a proportion of the order of:
  5 to 200 mg of antihistamine compound,
  10 to 300 mg of an inhibitor of histidine decarboxylase such as tritoqualine.

The compositions of the invention may be presented in a form for transdermal application, for example an ointment for children, a form for oral administration, for example a slow release product, or in gastro-resistant tablet form or gum form. They may also be in spray, bronchial form or eye lotion form, or galenic forms with programmed mucosal and secondarily per os disintegration.

Therefore the different compositions of the invention can be administered by several routes chosen in accordance with the patient's pathological profile and age. For children, the patch form, syrup form or tablets to be dissolved in the mouth. The other forms, eye lotion or injection may also be used. In adults all galenic forms can be contemplated.

The advantage of a coupled galenic form also provides simplicity of treatment, patient compliance with the simplified treatment and therefore a more successful outcome.

The methods of the invention include preventing an allergic illness and not only pathological conditions. Subjects who include children who have parents suffering from particular allergy(s) could be the major target of this preventive treatment. Although not wishing to be bound by any theory, this is because children of parents who have suffered from allergies are, either through family history, or environmental induction, predisposed to allergies. Typically, such subjects will generate an increased population of TH2 cells. Therefore, by increasing the TH1 cell number by therapeutic means described in this invention, it is possible to prevent or reduce allergic symptoms from developing or further developing. Treating such subjects would result in shorter hospital stays, fewer antibiotic treatments, and improved quality of life. Indeed, advantageously, the TH2/TH 1 switch should occur as early as possible in order to be effective, since in infants it is the TH2 route which predominates, responsible for hyper-response to the environment. The TH2/TH1 switch should occur early for its duration to be as long as possible, since antigenic stimulation by the antigens of the environment (dust mites and bacteria) are stimulators of the TH2 route.

Additional Dose Forms

The pharmaceutical compositions of the invention may be formulated as solid dosage forms, such as capsules, pills, softgels, tablets and troches. The pharmaceutical compositions of the invention may be formulated as liquid dosage forms.

The tablets, pills, capsules, softgels, troches and the like can contain one or more of the following ingredients, or compounds of a similar nature: a binder; a lubricant; a diluent; a glidant; a disintegrating agent; a coloring agent; a sweetening agent; a flavoring agent; a wetting agent; an emetic coating; and a film coating.

Examples of binders include microcrystalline cellulose and cellulose derivatives, gum tragacanth, glucose solution, acacia mucilage, gelatin solution, molasses, polyinylpyrrolidine, povidone, crospovidones, sucrose and starch paste.

Lubricants include talc, starch, magnesium or calcium stearate, *lycopodium* and stearic acid.

Diluents include, for example, lactose, sucrose, starch, kaolin, salt, mannitol and dicalcium phosphate.

Glidants include, but are not limited to, colloidal silicon dioxide, talc, corn starch.

Disintegrating agents include crosscarmellose sodium, sodium starch glycolate, alginic acid, corn starch, potato starch, bentonite, methylcellulose, agar and carboxymethylcellulose.

Coloring agents include, for example, any of the approved certified water soluble FD and C dyes, mixtures thereof; and water insoluble FD and C dyes suspended on alumina hydrate.

Sweetening agents include sucrose, lactose, mannitol and artificial sweetening agents such as saccharin, and any number of spray dried flavors.

Flavoring agents include natural flavors extracted from plants such as fruits and synthetic blends of compounds which produce a pleasant sensation, such as, but not limited to peppermint and methyl salicylate.

Wetting agents include propylene glycol monostearate, sorbitan monooleate, diethylene glycol monolaurate and polyoxyethylene laural ether.

Enteric-coatings include fatty acids, fats, waxes, shellac, ammoniated shellac and cellulose acetate phthalates. Film coatings include hydroxyethylcellulose, sodium carboxymethylcellulose, polyethylene glycol 4000 and cellulose acetate phthalate.

The compound, or pharmaceutically acceptable derivative thereof, could be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar and other enteric agents.

The compounds can also be administered as a component of an elixir, suspension, syrup, wafer, sprinkle, chewing gum or the like. A syrup may contain, in addition to the active compounds, sucrose as a sweetening agent and certain preservatives, dyes and colorings and flavors.

The active materials can also be mixed with other active materials which do not impair the desired action, or with materials that supplement the desired action, such as antacids, H2 blockers and anti-inflammatory agents. The active ingredient is a compound or pharmaceutically acceptable derivative thereof as described herein. Higher concentrations, up to about 98% by weight of the active ingredient may be included.

Tablets and capsules formulations may be coated as known by those of skill in the art in order to modify or sustain dissolution of the active ingredient. Thus, for example, they may be coated with a conventional enterically digestible coating, such as phenylsalicylate, waxes and cellulose acetate phthalate.

Agents of the invention may be administered to mammalian subjects, including: humans, monkeys, apes, dogs, cats, cows, horses, rabbits, mice and rats.

Agents of the invention may be administered orally, rectally, parenterally, intracisternally, intravaginally, intraperitoneally, topically (as by powders, ointments, gels, drops, transdermal patch or transcutaneous patch), bucally, in bronchial form or as an oral or nasal spray. The term "parenteral" as used herein refers to modes of administration which include intravenous, intramuscular, intrasternal, subcutaneous, intracutaneous, intrasynovial, intrathecal, periostal, intra-articular injection and/or infusion. Alternative methods include administration by implantable pump or continuous infusion, injection, or liposomes. Administration can be performed daily, weekly, monthly, every other month, quarterly or any other schedule of administration as a single dose injection or infusion, multiple doses, or in continuous dose form.

In yet an additional embodiment, the agents of the invention can be delivered by way of a pump.

For parenteral administration, in one embodiment, the agents of the invention are formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. For example, the formulation preferably does not include oxidizing agents and other compounds that are known to be deleterious to the agents of the invention.

The selected nucleic acid sequences are inserted into a single vector or separate vectors. More than one gene encoding a selected allergen, or portion thereof, may be inserted into a single vector or into separate vectors for introduction into the host cells. Alternatively, these sequences can be administered as naked nucleic acid sequences or as part of a complex with other molecules, e.g. liposomes.

The nucleic acid may be introduced in a suitable delivery vehicle such as an expression vector or encapsulation unit such as a liposome, or may be introduced directly through the skin, for example in a DNA vaccine.

Vectors suitable for use in the methods of the present invention are viral vectors including adenoviruses, lentivirus, retroviral vectors, adeno-associated viral (AAV) vectors.

Generally, the formulations are prepared by contacting the agents of the invention uniformly and intimately with liquid carriers/excipients or finely divided solid carriers/excipients or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes. Typical excipients for softgels include gelatin for the capsule and oils such as soy oil, rice bran oil, canola oil, olive oil, corn oil, and other similar oils; glycerol, polyethylene glycol liquids, vitamin E TPGS as a surfactant and absorption enhancer (Softgels: Manufacturing Considerations; Wilkinson P, Foo Sog Hom, Special Drug Delivery Systems; Drugs and the Pharmaceutical Sciences Vol 41 Praveen Tyle Editor, Marcel Dekker 1990, 409-449; Pharmaceutical Dosage Forms and Drug Delivery by Ansel, Popovich and Allen 1995, Williams and Wilkins, Chapter 5 pp 155-225). Tritoqualine and anti H1 may form either a solution in a selected oil vehicle or a suspension of fine particles (comprising any of the excipients disclosed herein, e.g., typical excipients for softgels).

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulin; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, manose, or dextrins; chelating agents such as EDTA; sugar alcohols such as mannitol or sorbitol; counterions such as sodium; and/or nonionic surfactants such as polysorbates, poloxamers, or PEG.

Any pharmaceutical used for therapeutic administration can be sterile. Sterility is readily accomplished by filtration through sterile filtration membranes (e.g., 0.2 micron membranes). Therapeutics generally are placed into a container having a sterile access port, for example, an intravenous solution bag or vial having a stopper pierceable by a hypodermic injection needle.

The manner in which the compounds are administered can vary. The compounds can be administered by inhalation (e.g., in the form of an aerosol, e.g., nasally); topically (e.g., in lotion form); orally (e.g., in liquid form within a solvent such as an aqueous or non-aqueous liquid, or within a solid carrier); intravenously (e.g., within a dextrose or saline solution); as an infusion or injection (e.g., as a suspension or as an emulsion in a pharmaceutically acceptable liquid or mixture of liquids); intrathecally; intracerebroventricularly; or transdermally (e.g., using a transdermal patch).

Although it is possible to administer the compounds in the form of a bulk active chemical, it is preferred to present each compound in the form of a pharmaceutical composition or formulation for efficient and effective administration. Exemplary methods for administering such compounds will be apparent to the skilled artisan. For example, the compounds can be administered in the form of a tablet, a hard gelatin capsule or as a time-release capsule. As another example, the compounds can be delivered transdermally using the types of patch technologies available from Novartis and Alza Corporation. The administration of the pharmaceutical compositions of the present invention can be intermittent or at a gradual, continuous, constant or controlled rate to a subject (e.g., a mammal such as a human, mouse, rat, cat, rabbit, dog, pig, cow, or monkey), but advantageously is administered preferably to a human being.

In addition, the time of day and the number of times per day that the pharmaceutical formulation is administered can vary.

The appropriate dose of the compound is that amount effective to prevent occurrence of the symptoms of the allergic reaction or to treat some symptoms of the allergic reaction from which the patient suffers. By "effective amount", "therapeutic amount" or "effective dose" is meant that amount sufficient to elicit the desired pharmacological or therapeutic effects, thus resulting in effective prevention or treatment of the disorder. Prevention of the allergic reaction is manifested by delaying the onset of the symptoms of the allergic reaction. Treatment of the disorder is manifested by a decrease in the symptoms associated with the allergic reaction or an amelioration of the recurrence of the symptoms of the allergic reaction.

Methods of the Invention

The invention provides methods for inhibiting, preventing or treating allergic reactions in a subject. The method comprises administering to a subject any of the agents of the invention to treat allergic reactions. The agents of the invention may be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the compounds or agents given first, followed by the second, and or third agent.

The agents of the invention may be administered alone or in combination with other therapeutic agents. Combinations may be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the compounds or agents given first, followed by the second.

Advantageously, the pharmaceutical composition of the invention is in a dosage form with controlled mucosal or sublingual controlled release and secondarily per os disintegration and/or release [e.g., controlled release].

The pharmaceutical composition of the invention is also useful for the preparation of a medicinal product intended to treat or prevent allergic hypersensitivity reactions, to treat or prevent allergic asthma, allergic rhinitis and atopic and allergic eczema.

Finally the pharmaceutical composition of the invention is particularly useful for the preparation of a medicinal product intended to treat or prevent allergic symptoms in children, infants and adults.

Dosages

Dosage of a therapeutic agent is dependant upon many factors including, but not limited to, the type of tissue affected, the type of disease being treated, the severity of the disease, a subject's health and response to the treatment with the agents. Accordingly, dosages of the agents can vary depending on each subject and the mode of administration.

The allergens may be administered to a subject in an amount and for a time (e.g. length of time and/or multiple times) sufficient to slow down the immunological response leading to increased IgE synthesis, in the subject. In an embodiment, 1 to 1500 ug and advantageously from 10 to 150 ug of allergen may be administered to a subject daily, weekly, monthly and/or yearly, in single or multiple times per day/week/month/year, depending on need. For example, in one embodiment, the allergen may initially be administered once every two weeks for a month, and then once every month thereafter.

The antihistamine may be administered in an amount from about 1 to 2000 mg weight of the patient/day. Alternatively, 5 to 200 mg of antihistamine compound may be given to a subject. Suitable amounts of antihistamine are described supra.

Inhibitors of histidine synthesis may be administered in an amount from about 1 to 2000 mg, preferably 10 to 300 mg, to a subject.

Kits of the Invention

In a further embodiment of the invention, the present invention provides kits (i.e., a packaged combination of reagents with instructions) containing the agents of the invention useful for inhibiting, preventing or treating allergic reactions.

The kit can contain a pharmaceutical composition that includes one or more agents of the invention effective for inhibiting, preventing or treating allergic reactions, and an acceptable carrier or adjuvant, e.g., pharmaceutically acceptable buffer, such as phosphate-buffered saline, Ringer's solution or dextrose solution. It may further include other materials desirable from a commercial and user standpoint, including other buffers, diluents, filters, needles, syringes, and package inserts with instructions for use.

The agents may be provided as dry powders, usually lyophilized, including excipients that upon dissolving will provide a reagent solution having the appropriate concentration.

The kit comprises one or more containers with a label and/or instructions. The label can provide directions for carrying out the preparation of the agents for example, dissolving of the dry powders, and/or treatment for a specific allergic reaction.

The label and/or the instructions can indicate directions for in vivo use of the pharmaceutical composition. The label and/or the instructions can indicate that the pharmaceutical composition is used alone, or in combination with another agent to treat an allergic condition.

The label can indicate appropriate dosages for the agents of the invention as described supra.

Suitable containers include, for example, bottles, vials, and test tubes. The containers can be formed from a variety of materials such as glass or plastic. The container can have a sterile access port (for example the container can be an intravenous solution bag or a vial having a stopper pierceable by a needle such as a hypodermic injection needle).

ADVANTAGES OF THE INVENTION

In one embodiment, the invention may be achieved by treating the two main pathways of the immune reaction:
firstly the upstream pathway of the immune response which, after presenting the antigen to the APCs leads to increased synthesis of the IgEs responsible for the self-recruiting of the immunity cells, and
secondly, the downstream pathway of the immune response which leads to release of the preformed mediators, essentially histamine, responsible for the final clinical outcome.

The optional combined use of an inhibitor of histamine synthesis makes it possible to reduce the amount of histamine produced by the and therefore to improve the therapeutic efficacy of the pharmaceutical composition according to the invention.

EXAMPLES

Example 1

Cystine Protease (DerP1)+Anti H1

One hundred patients were given a composition of the invention associating at least one allergen (i.e., DerP1® (50 µg/per day) and an antihistamine compound, and an H1 antagonist (also referred to herein as an inhibitor of histamine synthesis) (each patient utilized one dose of either loratadine 10 mg, ceterizine 10 mg, or fexofenadine 120 mg). Patients took only one type of anti H1 during the entire treatment period. The DerP1 is a liquid extract from the acarid species containing cystine protease delivered sublingually (purchased from Stallergen, 6, rue Alexis de Tocqueville 92183 Antony Cedex FRANCE). A commercial oral spray formulation 50 µg (four puffs) per day was used. Treatments were given once a day for six months.

Patient age ranged from 7 to 60 years of age. They all presented with at least one positive dust mite or pollen prick test, and symptomotology of rhinitis or asthma of at least one year's onset.

The pathological profile of the patients was classified according to the following typology comprising three descriptive categories: inflammation, secretion and the figured element.
Only clinical examination was used to classify inflammation. It was considered that there was inflammation if examination of the mucosa or target organs showed redness confirming an inflammatory phenomenon.
Secretion concerned the observation of an exudate whether purulent or non-purulent affecting a target organ (mucosa, skin, etc.).
The figured element concerned a change in the structure of the organ under consideration, which may occur in several pathological forms. Consideration was only given to the existence of a change without going into the detail of this change.

The grading of pathological severity used a scale of 1 to 4 measuring intensity as a fraction (¼ or ½) or a whole number. Therefore, according to this grading, an assessment of ¼ denotes target organ impairment of between 0 and less than ¼. An assessment of ½ denotes target organ impairment of between ¼ and one half; an assessment of ¾ denotes target organ impairment of more than one half and less than ¾; an assessment of 1 denotes impairment of more than ¾.

A first category of target organs was graded according to this typology. It comprised the eyes, nose, pharynx, larynx and the skin.

For grading of the lungs, the results of functional respiratory investigation were expressed as a percentage relative to the normal value (using an international classification method taking into account age and size in particular).

The patients were followed with at least one consultation at 2 months, 8 months, 12 months, and 24 months. Table I below gives a clear indication of the very positive results obtained after a treatment time of approximately 8 months. A distinct improvement was noted in the pathological condition of the patients, with a drop in the overall clinical score for severity falling from an average value of 9.56 to 2.47, the standard deviation decreasing from 1.15 to 0.53, confining the efficacy of the treatment in all patient age and sex groups. The mean number of affected target organs fell from 3.69 to 1.73, while the standard deviation in the number of target organs affected was reduced from 0.49 to 0.41.

TABLE 1

| Patient reference | Sex | Date of birth | Date of initial consultation | N° (#) of tests+ | Initial consultation | | 3rd consultation after 8 months' treatment | |
|---|---|---|---|---|---|---|---|---|
| | | | | | N° of target organs affected | Total clinical score | N° of target organs affected | Total clinical score |
| 1 | M | 1964 | 1996 | 3 | 3 | 7 | 2 | 2 |
| 2 | F | 1936 | 2000 | 4 | 3 | 6 | 1 | 2 |
| 3 | F | 1944 | 1993 | 8 | 4 | 10 | 2 | 2 |
| 4 | F | 1974 | 1997 | 8 | 4 | 9 | 1 | 3 |
| 5 | F | 1950 | 1997 | 8 | 4 | 9 | 2 | 3 |
| 6 | M | 1960 | 1997 | 7 | 4 | 8 | 1 | 2 |
| 7 | F | 1944 | 1996 | 4 | 3 | 6 | 2 | 2 |
| 8 | F | 1963 | 1993 | 4 | 5 | 10 | 1 | 2 |
| 9 | M | 1988 | 1993 | 7 | 4 | 8 | 2 | 2 |
| 10 | M | 1991 | 1993 | 3 | 4 | 9 | 1 | 2 |
| 11 | M | 1971 | 2000 | 6 | 3 | 9 | 1 | 2 |
| 12 | M | 1948 | 2000 | 3 | 4 | 9 | 1 | 2 |
| 13 | M | 1929 | 2000 | 3 | 3 | 7 | 2 | 2 |
| 14 | M | 1953 | 1999 | 5 | 4 | 9 | 1 | 1 |
| 15 | F | 1932 | 1994 | 10 | 4 | 10 | 1 | 2 |
| 16 | F | 1934 | 1996 | 8 | 6 | 11 | 2 | 2 |
| 17 | F | 1982 | 1993 | 5 | 4 | 10 | 2 | 2 |
| 18 | F | 1968 | 1994 | 4 | 4 | 10 | 2 | 2 |
| 19 | M | 1996 | 1996 | 4 | 4 | 10 | 1 | 3 |
| 20 | F | 1991 | 1997 | 5 | 4 | 10 | 2 | 3 |
| 21 | F | 1990 | 1996 | 7 | 3 | 8 | 1 | 2 |
| 22 | F | 1949 | 2000 | 4 | 4 | 8 | 2 | 3 |
| 23 | M | 1995 | 2000 | 3 | 2 | 6 | 1 | 2 |
| 24 | F | 1961 | 1994 | 8 | 3 | 8 | 1 | 2 |
| 25 | M | 1987 | 1994 | 7 | 4 | 9 | 2 | 3 |
| 26 | F | 1991 | 1995 | 8 | 3 | 8 | 1 | 2 |
| 27 | M | 1967 | 1994 | 7 | 3 | 9 | 2 | 2 |
| 28 | M | 1989 | 1994 | 7 | 4 | 9 | 2 | 3 |
| 29 | M | 1947 | 1999 | 5 | 4 | 9 | 2 | 2 |
| 30 | F | 1920 | 1999 | 2 | 3 | 8 | 1 | 2 |
| 31 | F | 1963 | 1997 | 6 | 4 | 9 | 2 | 2 |
| 32 | M | 1979 | 1998 | 4 | 4 | 9 | 1 | 2 |
| 33 | F | 1983 | 2000 | 3 | 3 | 8 | 2 | 2 |
| 34 | M | 1996 | 1999 | 7 | 4 | 8 | 2 | 2 |
| 35 | F | 1946 | 1995 | 7 | 3 | 8 | 2 | 3 |
| 36 | F | 1958 | 1995 | 5 | 4 | 10 | 2 | 2 |
| 37 | F | 1946 | 1997 | 6 | 4 | 11 | 2 | 2 |
| 38 | F | 1965 | 1993 | 3 | 3 | 9 | 1 | 2 |
| 39 | M | 1973 | 2000 | 7 | 4 | 9 | 2 | 2 |
| 40 | M | 1957 | 1995 | 5 | 4 | 9 | 2 | 2 |
| 41 | F | 1942 | 1995 | 8 | 4 | 9 | 2 | 2 |
| 42 | F | 1933 | 1999 | 4 | 3 | 9 | 1 | 3 |
| 43 | F | 1959 | 1999 | 4 | 3 | 8 | 2 | 3 |
| 44 | F | 1965 | 1999 | 3 | 4 | 10 | 2 | 2 |
| 45 | F | 1944 | 1999 | 3 | 4 | 10 | 2 | 3 |
| 46 | F | 1942 | 1996 | 6 | 4 | 11 | 1 | 3 |
| 47 | F | 1948 | 1997 | 6 | 4 | 11 | 2 | 3 |
| 48 | F | 1963 | 1999 | 4 | 4 | 10 | 2 | 2 |
| 49 | M | 1981 | 1999 | 5 | 4 | 12 | 2 | 2 |
| 50 | M | 1995 | 2000 | 5 | 4 | 12 | 2 | 2 |
| 51 | M | 1989 | 1999 | 5 | 4 | 10 | 2 | 2 |
| 52 | M | 1997 | 1998 | 4 | 4 | 10 | 2 | 3 |
| 53 | F | 1997 | 1998 | 5 | 4 | 9 | 1 | 3 |
| 54 | F | 1995 | 1997 | 4 | 4 | 10 | 2 | 3 |
| 55 | F | 1984 | 1993 | 3 | 3 | 9 | 1 | 2 |
| 56 | M | 1969 | 1996 | 10 | 4 | 12 | 2 | 3 |
| 57 | M | 1951 | 1996 | 11 | 4 | 11 | 2 | 2 |
| 58 | M | 1992 | 1997 | 5 | 4 | 11 | 2 | 3 |
| 59 | M | 1975 | 1994 | 4 | 3 | 9 | 1 | 2 |
| 60 | M | 1977 | 2000 | 5 | 4 | 12 | 2 | 3 |
| 61 | M | 1989 | 1993 | 5 | 4 | 12 | 2 | 3 |
| 62 | M | 1994 | 1998 | 8 | 4 | 11 | 2 | 3 |
| 63 | F | 1993 | 1998 | 7 | 4 | 10 | 2 | 2 |
| 64 | F | 1988 | 1993 | 3 | 3 | 9 | 2 | 3 |
| 65 | F | 1940 | 1999 | 4 | 4 | 11 | 2 | 2 |
| 72 | F | 1951 | 2000 | 6 | 4 | 11 | 2 | 3 |
| 73 | F | 1956 | 1999 | 5 | 4 | 11 | 2 | 3 |
| 74 | M | 1982 | 1994 | 4 | 3 | 9 | 2 | 3 |

TABLE 1-continued

| Patient reference | Sex | Date of birth | Date of initial consultation | N° (#) of tests+ | Initial consultation N° of target organs affected | Initial consultation Total clinical score | 3rd consultation after 8 months' treatment N° of target organs affected | 3rd consultation after 8 months' treatment Total clinical score |
|---|---|---|---|---|---|---|---|---|
| 75 | F | 1944 | 1998 | 3 | 4 | 12 | 2 | 2 |
| 76 | F | 1992 | 1997 | 7 | 3 | 9 | 2 | 3 |
| 77 | M | 1997 | 1993 | 4 | 3 | 9 | 1 | 3 |
| 78 | F | 1955 | 1997 | 5 | 4 | 10 | 2 | 3 |
| 79 | F | 1996 | 1999 | 4 | 3 | 8 | 2 | 3 |
| 80 | F | 1936 | 1993 | 5 | 4 | 10 | 1 | 2 |
| 81 | M | 1949 | 1998 | 5 | 3 | 10 | 2 | 2 |
| 82 | M | 1966 | 1993 | 4 | 3 | 9 | 2 | 2 |
| 83 | F | 1963 | 2000 | 5 | 4 | 10 | 1 | 2 |
| 84 | F | 1954 | 1993 | 5 | 4 | 11 | 2 | 2 |
| 85 | F | 1995 | 2000 | 4 | 3 | 9 | 2 | 3 |
| 86 | M | 1988 | 1994 | 6 | 3 | 8 | 2 | 2 |
| 87 | F | 1969 | 1997 | 6 | 4 | 9 | 2 | 3 |
| 88 | M | 1963 | 1993 | 5 | 4 | 9 | 2 | 2 |
| 89 | M | 1994 | 1998 | 7 | 4 | 10 | 1 | 3 |
| 90 | F | 1992 | 1997 | 6 | 3 | 9 | 3 | 3 |
| 91 | M | 1988 | 1999 | 6 | 4 | 11 | 2 | 3 |
| 92 | M | 1955 | 1993 | 6 | 4 | 11 | 2 | 3 |
| 93 | M | 1944 | 1996 | 7 | 4 | 13 | 2 | 3 |
| 94 | M | 1986 | 1994 | 6 | 4 | 12 | 2 | 3 |
| 95 | M | 1954 | 1996 | 6 | 4 | 11 | 2 | 3 |
| 96 | F | 1989 | 1993 | 6 | 4 | 12 | 2 | 2 |
| 97 | M | 1965 | 1995 | 6 | 3 | 8 | 2 | 3 |
| 98 | M | 1986 | 1994 | 4 | 3 | 9 | 2 | 4 |
| 99 | F | 1956 | 1995 | 4 | 4 | 10 | 2 | 3 |
| 100 | F | 1944 | 1993 | 2 | 3 | 9 | 1 | 3 |
| 101 | F | 1995 | 1998 | 5 | 3 | 9 | 2 | 4 |
| 102 | M | 1960 | 1996 | 3 | 3 | 8 | 2 | 3 |
| 103 | F | 1928 | 1995 | 6 | 4 | 10 | 2 | 3 |

No of test mean number of treatments, i.e. the number of times the patients were examined and treated.

Table 2 below gives the mean clinical score and the standard deviation in the scores obtained.

TABLE 2

| | INITIAL VISIT | VISIT AT 8 MONTHS |
|---|---|---|
| MEAN CLINICAL SCORE | 9.56 | 2.47 |
| STANDARD DEVIATION IN SCORES | 1.15 | 0.53 |

Table 3 below illustrates the average number of target organs affected and the standard deviation in the number of target organs affected.

TABLE 3

| | INITIAL VISIT | VISIT AT 8 MONTHS |
|---|---|---|
| MEAN N° OF AFFECTED TARGET ORGANS (T. 0.) | 3.69 | 1.73 |
| STANDARD DEVIATION IN N° AFFECTED T.Os. | 0.49 | 0.41 |

Example 2

Cystine Protease+Anti H1

The health benefits of the cystine protease (DerP1)+anti H1 were assessed in a clinical study for Rhinitis and asthma with human subjects using Spirometry. This study evaluated the benefit of adding DerP1 (cystine protease) to the existing therapy (Inhaled corticosteroids such as Pulmicord® (Astra Zeneca, Wilmington, Del.) alone or in combination with an anti H1.

Two groups of patients were studied, one group using topical corticosteroids, 500 μg/per day (Corticoids (inhaled); Pulmicord®), wherein corticoids were inhaled and thus delivery was topical via the pulmonary mucosa), defined as the control group, and a second group using topical corticosteroids, (Corticoids (inhaled) 500 μg/per day) plus the combination of cystine protease (DerP1, Stallergen Inc. (6, rue Alexis de Tocqueville 92183 Antony Cedex FRANCE)), DerP1 (an extract containing cystine protease) as an oral spray formulation and delivered sublingually, 50 μg/per day (4 puffs), and an antagonist H1 (each patient utilized one dose of either loratadine 10 mg, ceterizine 10 mg, or fexofenadine 120 mg). Patients took only one type of anti H1 during the entire treatment period.

The treatment group contained a total of 100 patients, 56 female and 44 male, aged 16-53. The Control group contained a total of 42 patents, 24 female and 18 male, aged 20-57 years of age. Patients in the control group were treated only by anti H1 (each patient utilized one dose of either loratadine [e.g., Claritin, Schering-Plough, New Jersey, USA; Alavert, Wyeth, New Jersey, USA] 10 mg, ceterizine [e.g., Zyrtec, Pfizer, New Jersey, USA] 10 mg, or fexofenadine [e.g., Allegra, Aventis, New Jersey, USA] 120 mg). Patients took only one type of anti H1 during the entire treatment period. Patients were selected based on positive response to Prick test and suffered from asthma and/or Rhinitis.

Each patient, according to height, weight, and age was assigned a normality value as defined in reference *Eur. Respir. J.* 1999; 13: 606-609, and the parameters FEV1 (Forced Expiratory Volume in One Second) and Raw (airway resistance) were determined at specified time intervals. Patients were followed, 6 (T1), 24 (T2), 48 (T3), and 72 (T4) weeks after the initiation (T0) of the treatment.

Illustrated on Tables 4 and 5 are the results of the study, which suggest that patients treated with DerP1+antiH1 showed significant improvement regarding the FEV1 (Forced Expiratory Volume in One Second) and Raw (Resistance Airways) parameters.

Table 4 illustrates that patients treated with the combination of DerP1+anti H1 improved approximately 15% in their FEV 1 parameter in 72 weeks of treatment compared to 4% of the control.

Table 5 illustrates a 45% improvement in RE (RAW evolution) parameter for the same period of treatment, compared to only 19% of the control group.

TABLE 4

| FEV1 | DerP1 + antiH1 % normality | Control % normality |
|---|---|---|
| T0 (start) | 92 | 90 |
| T1 (6)* | 94 | 96 |
| T2 (24)* | 102 | 93 |
| T3 (48)* | 108 | 95 |
| T4 (72)* | 108 | 94 |

*Weeks of treatment

TABLE 5

| RE | DerP1 + antiH1 % normality | Control % normality |
|---|---|---|
| T0 (start) | 222 | 215 |
| T1 (6)* | 185 | 180 |
| T2 (24)* | 160 | 175 |
| T3 (48)* | 140 | 178 |
| T4 (72)* | 120 | 173 |

*Weeks of treatment

Example 3

Cystine Protease+Tritoqualine

The health benefits of the cystine protease (or DerP1)+tritoqualine were assessed in a clinical study with human subjects using Spirometry. Two groups of patients (the treatment group was comprised of 50 patients 24 males and 26 females aged 14-41 years of age; the control group was comprised of 22 patients 12 females and 10 males aged 14-39 years of age) were studied, one group using topical corticosteroids (Corticoids (inhaled), Pulmicord®, Astra Zeneca, 500 µg/per day) defined as the control group, and a second group using topical corticosteroids, (Corticoids (inhaled), Pulmicord®, Astra Zeneca 500 µg/per day) plus the combination of cystine protease (or DerP1), sublingual spray, 50 µg/per day, and tritoqualine (200 mg daily).

Each patient, according to height, weight, and age was assigned a normality value defined in reference Eur Respir J 1999; 13: 606-609, and the parameters FEV1 and RAW, defined in example 2, were determined at specified time intervals. Patients were followed, 6 (T1), 24 (T2), 48 (T3), and 72 (T4) weeks after the initiation (T0) of the treatment. Results of the study as illustrated in Tables 6 and 7, suggest that patients treated with DerP1+tritoqualine showed significant improvement regarding the FEV1 and RAW parameters. Both Tables 6 and 7 show that there was a more dramatic improvement in FEV1 and RE (Respiratory evolution) approaching 100% normality or better. Table 6 illustrates that patients treated with the combination of DerP1+tritoqualine improved approx 32% in their FEV 1 parameter in 72 weeks of treatment compared to 23% of the control group and Table 7 illustrates a 42% improvement in Raw parameter for the same period of treatment, compared to 33% of the control group.

TABLE 6

| FEV1 | DerP1 + tritoqualine % normality | Control % normality |
|---|---|---|
| T0 (start) | 65 | 63 |
| T1 (6)* | 80 | 79 |
| T2 (24)* | 85 | 81 |
| T3 (48)* | 89 | 82 |
| T4 (72)* | 96 | 82 |

*Weeks of treatment

TABLE 7

| Raw | DerP1 + tritoqualine % normality | Control % normality |
|---|---|---|
| T0 (start) | 55 | 53 |
| T1 (6)* | 68 | 68 |
| T2 (24)* | 75 | 76 |
| T3 (48)* | 87 | 80 |
| T4 (72)* | 95 | 80 |

*Weeks of treatment

Example 4

The objective of this report is to demonstrate the efficiency of combining a single allergen with an antagonist H1 and a histamine synthesis inhibitor in managing allergic patients.

The clinical scores and respiratory airway measurement were consigned on each patient report form and were significantly improved over treatment period.

Methodology/Inclusion Criteria

Patients 16-60 year old were selected; each had a history of allergic disease equal or superior to 2 years; each were previously treated with classical antagonist H1 and local therapeutics without appropriate results, motivating the patient to seek new therapy; these patients had rhino-conjunctivitis associated with respiratory signs; and each were Prick test positive for at least 2 tests from the following list: Acarid: *Dermatophagoide Farinae, Dermatophagoide Ptéronyssinus*, Moulds: *Alternaria, Mucor, Aspergillus*, Dog, Cat dander, pollen of trees: *Bétulae*, fagaes, Cupressaceous, pollen of grass: Herbacees1, Herbacées2, Herbacées3, Rye grass, and other: latex, feather, mustard, egg, groundnut.

The Clinical score was set to be superior to 8 at the initial visit and is calculated as shown in Table 8:

TABLE 8

| | SCORE | | | |
|---|---|---|---|---|
| | Inflammation | Secretion | Structural modification | Average |
| Rhinitis | 3 | 3 | 3 | 3 |
| Laryngitis | 1 | 1 | 1 | 1 |

TABLE 8-continued

|  | SCORE | | | |
| --- | --- | --- | --- | --- |
|  | Inflammation | Secretion | Structural modification | Average |
| Eyes | 3 | 3 | 3 | 3 |
| Skin | 2 | 1 | 3 | 2 |
| Average Total |  |  |  | 9 |

Three physical criteria were evaluated:
Inflammation: this criterion corresponds to the observation of a macroscopic redness
Secretion: This criterion corresponds to the observation of a macroscopic secretion
Structural modification: this criterion corresponds to morphological modifications of the observed organ.
5 levels of severity: from 0 to 4 were attributed, as follows:
0 no inflammation, secretion or structural modification
1 target organ surface area<25%
2 target organ surface area 25% to 50%
3 target organ surface area 50% to 75%
4 target organ surface area>75%

Design
    Patients were observed at T0 initial visit
    at T1 (+6-8 weeks)
    at T2 (+24-30 week from T0)
Treatments
Group A: Patients were treated initially with H1 antagonists (DerP1) at T0, then adding to the H1 antagonist a single allergen at 300 IR, 10 drop as the daily dose (supplier ALLERBIO or STALLERGENES) from T1 and prescribed till the T2 visit (See Table 9).
Group B: Patients were treated initially with the combination of H1 antagonists+histamine synthesis inhibitor at T0, then adding the same single allergen at the same daily dose of 10 drops from T1 and prescribed till the T2 visit (see Table 9).
H1 Antagonists were prescribed at their recommended daily dosage (Vidal, edition 1997). Histamine synthesis inhibitor (Hypostamine®=tritoqualine, Chiesi laboratories, Italy), was prescribed at the fixed daily dose of 200 mg.

TABLE 9

|  | T0 | T1 | T2 |
| --- | --- | --- | --- |
| Group A | antagonist H1 | antagonist H1 + single allergen | antagonist H1 + single allergen |
| Group B | antagonist H1 + tritoqualine | antagonist H1 + tritoqualine + single allergen | antagonist H1 + tritoqualine + single allergen |

The clinical evaluation and scoring, the prick test, the spirometry parameters, and blood tests (IgE, IgA, IgM IgG, Ferritine, CRP) were performed at T0 (Table 10). Clinical scoring and spirometry were repeated at T1 and T2.
Concomitant local medications (see table below) were maintained for each patient

TABLE 10

|  | T0 | T1 | T2 |
| --- | --- | --- | --- |
| Rhinitis | Local corticoid or Cromone | Local corticoid or Cromone | Local corticoid or Cromone |
| Eyes | Local corticoid or Cromone | Local corticoid or Cromone | Local corticoid or Cromone |
| Skin | Local corticoid | Local corticoid | Local corticoid |

TABLE 10-continued

|  | T0 | T1 | T2 |
| --- | --- | --- | --- |
| Lung | Inhalated corticoid or Beta 2 mimetic | Inhalated corticoid or Beta 2 mimetic | Inhalated corticoid or Beta 2 mimetic |

Adverse Effects

|  | Antagonist H1 | Hypostamine | Single allergen |
| --- | --- | --- | --- |
|  | Sleep disturbances | Digestive disorders | Pruritus Increased symptomatology Rhinitis, cough |
| Conclusion | Low frequency | Very rare | Rare |

Statistical Analysis
Analysis of average, variance and Ki2 test are made for the 2 groups, including calculation of confidence intervals.
Results
Demographic characteristics are shown in Table 11

TABLE 11

|  | Age | Average | Interval | Female | Male |
| --- | --- | --- | --- | --- | --- |
| Group A 656 | 16-60 | 42.44 | 14.32 | 394 | 262 |
| Group B 486 | 16-60 | 40.28 | 15.63 | 287 | 199 |
| Total |  |  |  | 681 | 461 |
| Percentage |  |  |  | 59.63 | 40.37 |

Clinical scoring and clinical characteristics at T0 shown in Table 12

TABLE 12

|  | Prick test + Target organ | | Initial clinical score |
| --- | --- | --- | --- |
| Group A 656 Average | 5.68 | 3.71 | 9.68 |
| Group A 656 Variance | 1.93 | 0.52 | 1.63 |
| Group B 486 Average | 4.88 | 3.81 | 9.56 |
| Group B 486 variance | 1.84 | 0.64 | 1.37 |

Clinical scoring at T1 shown in Table 13

TABLE 13

|  | Target organ | Clinical score |
| --- | --- | --- |
| Group A 656 Average | 3.21 | 7.1 |
| Group A 656 Variance | 0.63 | 1.45 |
| Group B 486 Average | 3.05 | 5.77 |
| Group B 486 variance | 0.54 | 1.17 |

Clinical scoring at T2 shown in Table 14.

TABLE 14

|  | Target organ | Clinical score |
| --- | --- | --- |
| Group A 656 Average | 2.76 | 5.32 |

TABLE 14-continued

| | Target organ | Clinical score |
|---|---|---|
| Group A 656 Variance | 0.43 | 0.98 |
| Group B 486 Average | 1.87 | 2.90 |
| Group B 486 Variance | 0.56 | 0.87 |

Efficacy: Comparison group A and B shown in Table 15.

TABLE 15

| Time | Group A 656 | Group B 486 | P |
|---|---|---|---|
| T0 | 9.68 | 9.56 | ns |
| T1 | 7.1 | 5.77 | 0.1 |
| T2 | 5.32 | 2.90 | 0.05 |

Spirometry results are shown in Table 16.

TABLE 16

| SPIROMETRY | Result | Result | Result |
|---|---|---|---|
| RAW | T0 | T1 | T2 |
| Group 656 | 235 | 227 | 210 |
| Group B 486 | 240 | 231 | 169 |
| P | NS | NS | 0.02 |

The examples are presented to demonstrate the present invention and to assist one of ordinary skill in using the same. The examples are not intended in any way to otherwise limit the scope of the disclosure of the protection granted by Letters Patent granted hereon.

What is claimed is:

1. A pharmaceutical composition, comprising:
   a. An antihistamine compound selected from a group consisting of brompheniramine, cetirizine, fexofenadine, cyproheptadine, dexchlorpheniramine, hydroxizine, ketotifen, loratadine, mequitazine, oxotomide, mizolastine, ebastine, astemizole, carbinoxamide, alimemazine, buclizine, cyclizine hydrochloride and doxylamine,
   b. a pollen allergen comprising at least one cysteine protease epitope wherein the epitope consisting of the amino acid sequence of SEQ ID NO: 3, SEQ ID NO: 4 or SEQ ID NO: 5 and
   c. a pharmaceutically acceptable carrier.

2. The pharmaceutical composition of claim 1, wherein the pollen allergen is a peptide consisting of the amino acid sequence of SEQ ID NO: 3, SEQ ID NO: 4 or SEQ ID NO: 5 or an isolated nucleic acid molecule encoding said peptide consisting of SEQ ID NO: 3, SEQ ID NO: 4 or SEQ ID NO: 5.

3. An antiallergic pharmaceutical composition, comprising:
   a. at least one antihistamine compound selected from the group consisting of brompheniramine, cetirizine, fexofenadine, cyproheptadine, dexchlorpheniramine, hydroxizine, ketotifen, loratadine, mequitazine, oxotomide, mizolastine, ebastine, astemizole, carbinoxamide, alimemazine, buclizine, cyclizine hydrochloride and doxylamine,
   b. tritoqualine,
   c. a pharmaceutically acceptable carrier, and
   d. a pollen allergen comprising at least one cysteine protease epitope wherein the epitope consisting of the amino acid sequence of SEQ ID NO: 3, SEQ ID NO: 4 or SEQ ID NO: 5.

4. The antiallergic pharmaceutical composition of claim 3, wherein the pollen allergen is a peptide consisting of the amino acid sequence of SEQ ID NO: 3, SEQ ID NO: 4 or SEQ ID NO: 5 or an isolated nucleic acid molecule encoding said peptide consisting of SEQ ID NO: 3, SEQ ID NO: 4 or SEQ ID NO: 5.

5. The pharmaceutical composition of claim 3, wherein the antihistamine compound is selected from the group consisting of mizolastine, carbinoxamide, alimemazine, buclizine and cyclizine hydrochloride.

* * * * *